United States Patent
Wells

Patent Number: 5,298,967
Date of Patent: Mar. 29, 1994

[54] MEASUREMENT OF CONCENTRATIONS OF DISSOLVED SOLVENT

[75] Inventor: David Wells, Arlington, Va.

[73] Assignee: Pacific Scientific Company, Newport Beach, Calif.

[21] Appl. No.: 892,026

[22] Filed: Jun. 2, 1992

[51] Int. Cl.$^5$ ............... G01N 15/02; G01N 30/02; G01N 1/28

[52] U.S. Cl. ............... 356/336; 356/338; 356/37; 73/61.72; 422/73; 422/110; 436/36; 436/164

[58] Field of Search ............... 356/335-336, 356/243, 37, 23, 72, 337, 339, 36, 338, 343, 340; 422/73, 110, 112, 115; 250/222.2, 574; 73/61.72, 64.56, 863, 864.81; 436/36, 164, 181

[56] References Cited

U.S. PATENT DOCUMENTS

| | | | |
|---|---|---|---|
| 3,705,770 | 12/1972 | Kashiki | 356/36 |
| 3,787,122 | 1/1974 | Lepper, Jr. | 356/338 |
| 3,854,321 | 12/1974 | Dahneke | 356/336 |
| 3,910,702 | 10/1975 | Corll | 356/73 |
| 4,173,415 | 11/1979 | Wyatt | 356/336 |
| 4,284,496 | 8/1981 | Newton | 356/72 |
| 4,361,400 | 11/1982 | Gray et al. | 356/23 |
| 4,449,816 | 5/1984 | Kohsaka et al. | 356/37 |
| 4,761,074 | 8/1988 | Kohsaka et al. | 356/336 |
| 4,794,086 | 12/1988 | Kasper et al. | 356/335 X |
| 4,842,406 | 6/1989 | VonBargen | 356/336 |
| 4,984,889 | 1/1991 | Sommer | 356/336 |
| 5,076,097 | 12/1991 | Zarrin et al. | 73/61.72 X |
| 5,098,657 | 3/1992 | Blackford et al. | 356/335 X |

*Primary Examiner*—Richard A. Rosenberger
*Assistant Examiner*—Hoa Q. Pham
*Attorney, Agent, or Firm*—Lane, Aitken & McCann

[57] ABSTRACT

In a system for measuring minute concentrations of dissolved solids in liquids, seed particles of a known diameter are mixed with the liquid and the mixture of the seed particles and the liquid is atomized into droplets of a known size. The droplets are dried to residue particles comprising the seed particle surrounded by a shell of the dissolved solid. The size of the residue particles are measured by passing the residue particles through a laser beam to scatter light to photodetectors so as to generate a pulse from each particle. The amplitude of the pulses will indicate the size of the residue particle from which the thickness of the shell and the concentration of the dissolved solid can be determined.

18 Claims, 4 Drawing Sheets

MEASUREMENT OF CONCENTRATIONS OF DISSOLVED SOLVENT

BACKGROUND OF THE INVENTION

This invention relates to a system for measuring minute quantities of solid materials and, more particularly, to a system for measuring minute concentrations of dissolved solids in liquids.

In the manufacture of semiconductor chips, super pure water and other solvents are needed. For example, in the manufacture of very large scale integrated (VLSI) circuits, the surface of the semiconductor wafer which is to become the VLSI circuit must be repeatedly washed or cleansed. Very pure water is used to wash the surface and any nonvolatile residue dissolved in the water will have a tendency to remain on the surface of the wafer when the ultrapure water has evaporated. Since minimal traces of residue material on the surface of the semiconductor wafer can cause defects in the resulting semiconductor device, it is imperative to use very pure water of the highest quality to prevent or eliminate possible defects. There is also a need for very pure water in other industries, such as in the pharmaceutical industry and in electric power generating. Water for pharmaceutical injectibles must be free from bacterial and pyrogens if it is not to cause pathological effects when injected into the human body. The electric power industry requires ultrapure water for high pressure steam generation to drive turbine generators because impurities in the water can be deposited on turbine blades and cause unbalancing of the turbine or cause corrosion. Accordingly, there is a need to be able to measure minute quantities of dissolved solvents in liquids to ensure that the liquid has the requisite purity for the application.

One effective system for measuring minute concentrations of dissolved solids and liquids in use prior to the present invention involves atomizing the liquid into droplets 10 to 100 microns in diameter, then drying the droplets to a residue in the form of a particle approximately spherical in shape. The size of the particle is then measured by passing the particle through a light beam to scatter light from the beam to photodetectors or photodetectors. The amplitude of the resulting pulse produced by the photodetector will provide a measurement of the diameter of the particle. If the size of the original droplet is known, the concentration of the dissolved solid in the liquid from which the droplet was formed can be determined.

The concentration of the solid in the liquid is related to the diameter of the residue particle and the droplet diameter in accordance with the following equation:

$$C = (d/D)^3 \qquad (1)$$

in which C is the concentration, d is the (1) residue particle diameter and D is the liquid droplet diameter. By making the liquid droplet bigger, a more minute concentration can be detected. However, droplets larger than 100 microns cannot be easily dried. As a practical matter to ensure reliability of the measurement, droplet sizes of around 50 microns are employed. If the concentration of the liquid were 1 part per million and the original droplet size were 50 microns, then the diameter of the residue particle would be about 0.5 microns which corresponds to the sensitivity of some relatively inexpensive particle detectors. Some higher quality particle detectors have a sensitivity to detect particles 0.3 microns in size. Assuming a 50 micron droplet since, such a particle detector can detect a concentration of $(0.3/50)^3$ or about 200 parts per billion. This sufficient sensitivity is not sufficient for VLSI circuits and some other applications. State of the art particle detectors can detect smaller particles and have sufficient sensitivity for VLSI application, but such particle detectors are many times for expensive than the particle detectors with a sensitivity to detect 0.3 micron particles.

SUMMARY OF THE INVENTION

The purpose of the present invention is to achieve satisfactory sensitivity in the detection of dissolved solids with moderately priced particle sensing instruments. In accordance with the present invention, a seed particle of known diameter is added to the atomized droplet before it is dried. The diameter of the seed particle is selected to be slightly larger than the sensitivity of the instrument for detecting particle size. When the atomized droplet is dried, the resulting residue particle, called a residue measurement particle, will have a diameter which is greater than the known diameter of the seed particle. The amount that the diameter of the residue particle is greater than the seed particle will provide an accurate indication of the amount of dissolved solid in the liquid with the measurement achieving a substantial greater sensitivity in the measurement of the concentration of the dissolved solid for the selected particle measuring. For example, if the original droplet size is 50 microns and the seed particle has a diameter of 0.343 microns, a dissolved solid concentration of about 19 parts per billion will cause an increase in the pulse amplitude over that which would be produced by the seed particle of about 10 percent. Thus, 19 parts per billion is comfortably measured by the instrument of the present invention using a particle detector with a sensitivity to detect 0.3 micron particles and without pushing any of the parameters to their limits. By decreasing the size of the droplets, or by decreasing the size of the seed particle and using a particle detector with greater sensitivity, much greater sensitivity of the instrument to dissolved solids can be obtained. By increasing the size of the atomized droplets, the sensitivity can also be increased.

To make accurate measurements, the rate of flow of the entrained particles through the laser beam and the intensity of the laser beam must be kept constant or variations in these parameters accounted for because the velocity of the particle passing through the laser beam and the intensity of the laser beam will affect the amplitude of the pulses generated by the photodetector detecting light scatter from the particles. In accordance with one embodiment of the present invention, the method of measurement is calibrated for variations in the flow rate or the intensity of the laser beam by forming a second liquid droplet with a much larger seed particle, called a monitor seed particle, in the droplet. The resulting residue particle, called a residue monitor particle, formed from the droplet with the monitor seed particle will be correspondingly larger. The size of the monitor seed particle is selected so that variations in the concentration of the dissolved solid to be measured will cause only a small variation in the size of the residue monitor particle. At the upper end of the calibration curve which relates the particle size to the pulse amplitude in the laser beam instrument measuring the particle size, the curve becomes substantially flat so that further increases in particle size do not result in increases in pulse amplitude. The size of the monitor seed particle is selected so that it will fall in this flat portion of the calibration curve. Thus, both because the size of the monitor seed particle is relatively large and because it occurs in the flat portion of the calibration curve, variations in the concentration of the dissolved solid to be measured will have substantially no effect on the pulse amplitude. On the other hand, the pulse amplitude will still vary substantially with both the flow rate of the air stream entraining the residue particles and also with the intensity of the laser beam. More specifically, a change in the flow rate or a change in the beam intensity will cause the same percentage change in the pulse amplitude for pulses generated from a residue measurement particle and from a residue monitor particle. Thus, the variations in the pulse amplitude generated by the residue monitor particles can be used to correct the measurements of the concentration of the dissolved solid generated from the smaller residue measurement particles for variations caused by changes in the flow rate or in the intensity of the laser beam.

In an alternative embodiment of the invention, an atomizer is employed having a plurality of chambers behind separate nozzles each capable of injecting droplets into a common drying column to dry the droplets. The liquid sample containing the dissolved solid mixed with the 0.343 micron beads is drawn through one of the nozzle chambers to be injected into the drying column. Another chamber in the atomizer receives ultrapure liquid mixed with calibration beads of the same 0.343 size and droplets from this chamber are also injected periodically into the drying column. When these droplets containing the calibration beads are dried and then detected by the particle size measurement instrument, these measurements provide a basis for an updated calibration of the instrument.

DESCRIPTION OF THE PREFERRED EMBODIMENT

Figure 1:
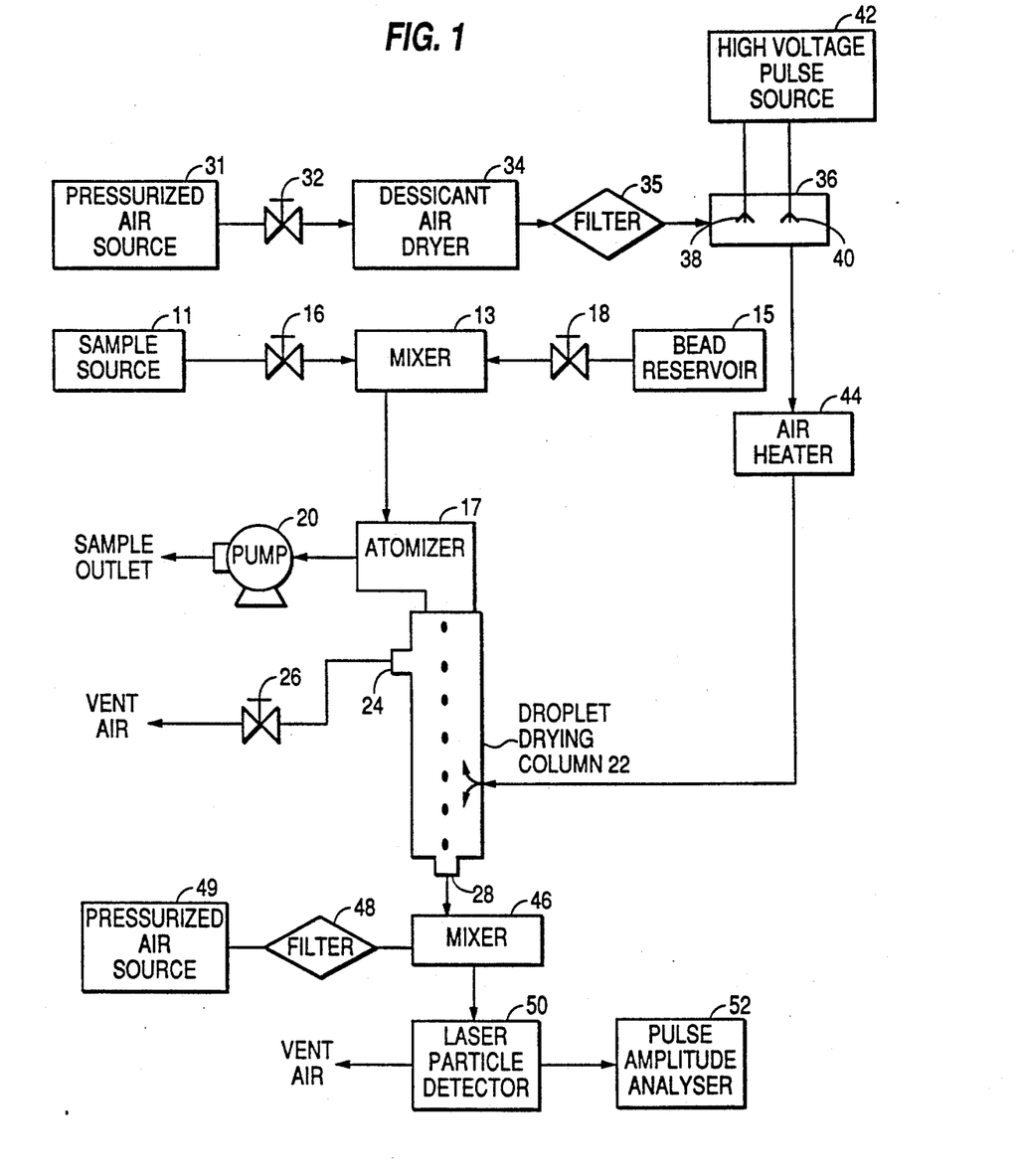
FIG. 1 schematically illustrates the method and system of the present invention.

As shown in FIG. 1, a sample of the liquid to be measured from a source 11 of the liquid sample is caused to flow into a mixer 13, which also receives spherical seed particles from a reservoir 15 of seed particles suspended in ultrapure water. The flow of the liquid sample and the seed particles into the mixer 13 is controlled by valves 16 and 18, respectively. The seed particles should be insoluble in the sample liquid and when the sample liquid is water, the seed particles, for example, may be latex beads. In the preferred specific embodiment, most of the latex beads have a diameter of 0.343 microns. A few of the latex beads, which are the monitor seed particles, have a diameter of 1.1 microns. From the mixer 13, the sample liquid entraining the spherical beads is caused to flow through an atomizer 17, which atomizes a portion of the sample stream containing the spherical beads into droplets, which are controlled to be 50 microns in diameter. A pump 20 is provided downstream from the atomizer 17 and, by negative pressure or suction, the pump 20 draws the sample from the sample source into the mixer 13, draws the beads from the reservoir 15 into the mixer 13 and draws the mixture of the beads and the sample through a chamber in the atomizer 17. As the mixture of beads and the liquid sample are drawn through the atomizer chamber, the atomizer atomizes a portion of the sample into droplets ejecting the droplets downwardly into a drying column 22.

Preferably, the beads are mixed into the liquid at a concentration of about 250,000,000 per milliliter so that most of the droplets ejected by the atomizer will contain one bead. Because of the randomness of the distribution of the beads in the liquid, some of the droplets ejected by the atomizer will have multiple beads and some of the droplets will have no beads, but, for the most part, each droplet will contain one latex bead. Preferably, the atomizer 17 is of the bubble jet type which is used in laser jet printers, but it also may be a vibrating orifice nozzle of the type provided in the equipment manufactured by TSI, Inc. or such as manufactured by Sonotec Corporation. Other types of atomizers which are known in the art and which would be suitable for use in this invention are the compressed air atomizer, the spinning disc atomizer and the spinning top atomizer.

Figure 2:
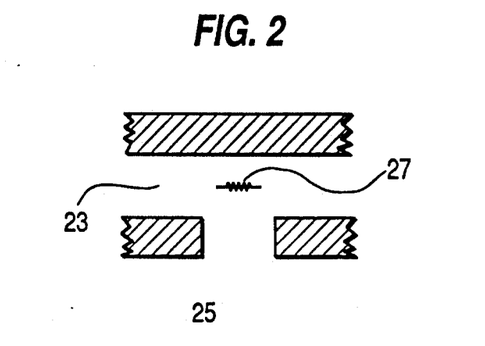
FIG. 2 schematically illustrates a portion of the atomizer employed in the system of the present invention to generate droplets of a precisely controlled size.

FIG. 2 is a sectional view schematically illustrating a portion of the atomizer showing one nozzle opening of the atomizer in section. As shown in FIG. 2, the mixture of the sample and the latex beads are drawn through a chamber 23 in the atomizer by pump 20. Nozzle opening 25 opens to the chamber 23 and extends vertically from the chamber 23 opening to the top of the drying column 22. A resistor 27 is positioned in the chamber 23 over the nozzle opening 25. To eject a droplet, a high energy electrical pulse is applied to the resistor 27, which becomes heated a converts a portion of the sample in the chamber 23 to a steam bubble. The pressure of the steam bubble ejects a droplet of the sample through the nozzle opening 25 and into the drying column 22. With this kind of nozzle, the diameter of the ejected droplet can be precisely controlled. Because the atomizer employed is identical to that used in printers, i.e., the Hewlett Packard Think Jet printer, the atomizer is commercially available at a low price. A typical low priced atomizer has 30 nozzle openings with a resistor in the chamber behind each nozzle opening. In accordance with the preferred embodiment of the present invention, four of these nozzle openings are used. The resistor behind the four selected nozzles are pulsed in sequence to cause droplets to be ejected from the four nozzle openings in sequence. A plurality of the nozzle openings are used in this manner to enable the atomizer to continue to be used should one of the nozzle openings become clogged.

Figure 3:
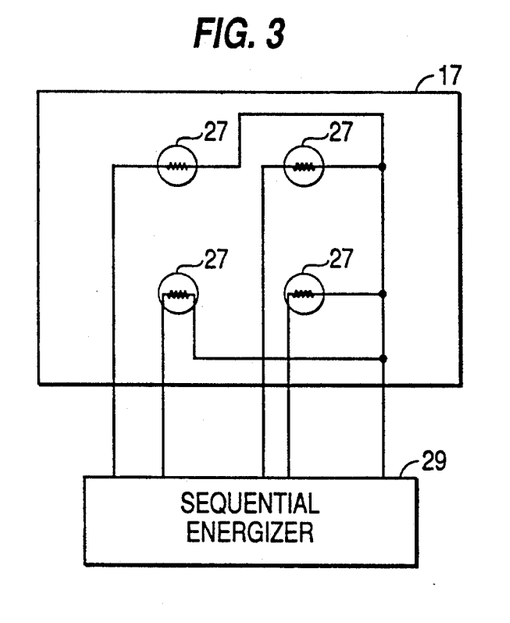
FIG. 3 schematically illustrates the system for controlling the atomizer to eject droplets in sequence from a plurality of different nozzles.
Figure 4:
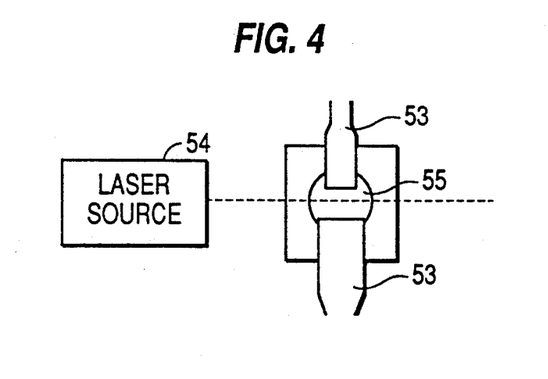
FIG. 4 schematically illustrates the particle detector employed in the present invention.
Figure 5:
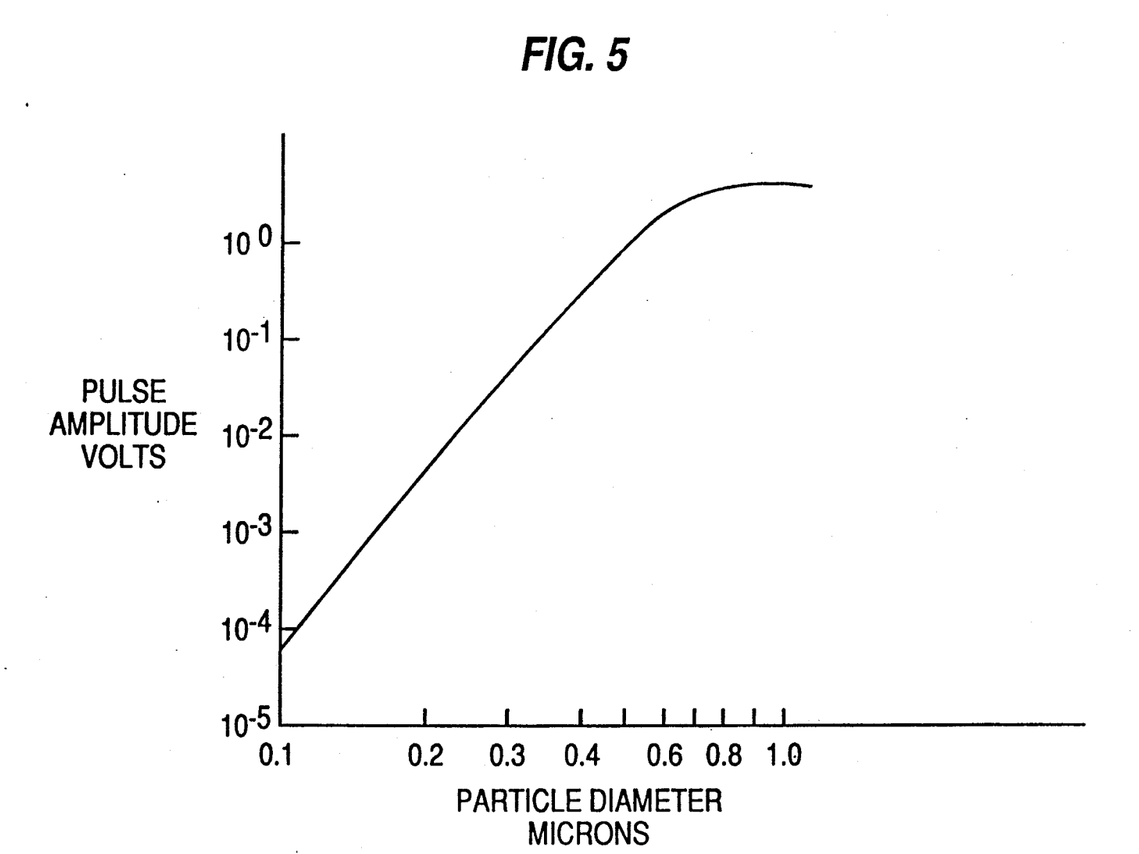
FIG. 5 is a curve illustrating how the pulse amplitude produced by the particle detector employed in the system of the present invention varies with particle size.

FIG. 3 schematically illustrates the nozzle sequencing system of the present invention. As shown in FIG. 3, a sequential energizer 29 applies pulses in sequences to four resistors 27 behind four of the nozzle openings in the atomizer 17 thus causing droplets to be ejected from the four nozzle openings in sequence. The bubble jet type atomizer nozzle for printing applications is described in *Output Hardware Devices*, Chapter 13, by William J. Lloyd and Howard H. Taub, published by Academic Press in 1984.

The drying column 22 is a cylindrical chamber with its axis positioned vertically. The column 22 serves the function of drying the droplets to residue particles, the function of neutralizing the static charges on the droplets, and the function of separating any smaller satellite droplets produced by the atomizer from the droplets having the precisely controlled size of 50 microns in diameter. Ionized drying air is introduced into the column 22 about a third of the way from the bottom of the column and drying air flows upwardly and downwardly from its point of introduction into the column. The ionized air contains both positive and negative charges and, as it passes over the droplets, it neutralizes any static electrical charge on the droplets.

In addition, the air in the column flowing upwardly from the point of introduction will separate smaller satellite droplets in the column from the 50 micron droplets and carry the satellite droplets up to an exhaust port near the top of the dryer column where the upwardly flowing air carrying the satellite droplets is exhausted from the column through a valve 26. The 50 micron droplets are injected into the column by the atomizer 17 with downward momentum and the upwardly flowing drying air in the column is unable to overcome the momentum of the 50 micron droplets. Accordingly, the 50 micron droplets pass through the upwardly flowing air to the lower part of the column. The satellite droplets, on the other hand, being lighter in weight than the 50 micron diameter droplets have insufficient momentum to overcome the upwardly flowing drying air in the upper part of the column and become entrained in this upwardly flowing air and are carried out through the exhaust port 24.

As the droplets pass through the upwardly flowing air and then through downwardly flowing air in the lower part of the column, the droplets are dried to their residue, which, in the case of most droplets, will be a spherical bead surrounded by a spherical shell of the dissolved solid in the sample liquid. The downward flow of air in the column 22 carries the dried residue particles out of an exhaust port 28 in the bottom of the column.

The drying air is supplied from a pressured source 31 through a regulating valve 32, a desiccant air dryer 34, and a filter 35 to an ionizing chamber 36. In the ionizing chamber 36, high voltage pulses alternating in polarity are applied to the air between electrodes 38 and 40 from a high voltage supply 42. The high voltage source 42 applies high voltage pulses between the electrodes 38 and 40 in the range of 4,000 to 10,000 volts at a frequency ranging from 0.5 to 5 cycles per second with the pulse polarity alternating on successive pulses. The high voltage applied to the air ionizes the air and the ionized air flows to an air heater 44. Heated air from the air heater 44 is directed into the ionized air inlet of the column 22. The ionized air will carry positive and negative charges on the individual air ions and these positive and negative charges will neutralize any static electricity charges on the droplets produced by the atomizer 17.

The ionizer comprising the ionizing chamber 36 and the high voltage supply 42 may be similar to that supplied by Static Control Services under the trademark PULSEBAR® and as described in the Static Control Services catalog.

The aerosol of the residue particles passing through the exhaust port 28 at the bottom of the drying column 22 enters a mixer 46 where the aerosol is mixed with diluting air supplied through a filter 48 from a source of pressurized air 49. The diluted aerosol then flows through a laser beam particle measuring instrument, which may be of the type manufactured by the Hiac Royco Division of Pacific Scientific Company and identified by Model No. 5230A. This particle measuring instrument has a sensitivity to detect particles down to 0.3 microns in size. The principle of operation of the particle measurement instrument is disclosed in U.S. Pat. No. 4,842,406 to Kenneth Paul VonBargen and in U.S. Pat. No. 4,984,889 to Holger T. Sommer. The instrument comprises a laser particle detector 50 in which the residue particles pass through a laser beam and a pulse amplitude analyzer 52, which measures the amplitude of each pulse. The atomizer 17 ejects droplets at a rate such that one particle at a time passes through the laser beam. As shown schematically in FIG. 4, the aerosol of residue particles is directed by nozzles 53 through a laser beam generated by a laser beam source 54. As each particle passes through the laser beam, it will scatter light to a photodetector 55 and the amplitude of the resulting pulse will be an indication of the size of the particle causing the pulse. The pulses produced by the photodetector are applied to the pulse amplitude analyzer 52 which measures the amplitude of each pulse produced by the photodetector. Each pulse amplitude is measured by determining an amplitude range into which the pulse falls and a counter is provided to count the number of pulses in each range. In this manner, the pulse amplitude of each pulse produced by a residue particle containing a 0.343 micron bead is measured and the amplitude of each pulse produced by a particle containing a 1.1 micron bead is also measured. The amplitude range into which pulses produced from the particles containing the 0.343 micron beads represents a corresponding size range of particles and represents a measurement of particle size. Particles consisting entirely of the dissolved solid residue will be much smaller and any pulses caused by these particles will be disregarded. In addition, pulses caused by particles containing more than one bead will be much larger and can be disregarded. The amplitude of pulses caused by residue particles each containing one 0.343 micron bead will provide an accurate measurement of the concentration of the dissolved solid in the sample liquid to about 19 parts per billion.

The Model 5230A particle measuring instrument, manufactured by the Hiac Royco Division of Pacific Scientific Company, has a sensitivity to measure particles down to 0.3 microns. This instrument has a signal-to-noise ratio of 2.76 for pulses produced in response to 0.343 micron particles, which means that this instrument is quite practical to measure sizes of particles on this order of magnitude. With this particle measuring instrument, a concentration of dissolved solids in the original liquid of 19 parts per billion can easily be detected as is explained below.

The size of a residue measurement particle can be represented by the following expression:

$$D_{grown} = (1+m)D_{seed} \qquad (2)$$

wherein $D_{grown}$ is the diameter of the residue measurement particle, $D_{seed}$ is the diameter of the measurement seed particle or 0.343 microns and m is the increase in the diameter of the residue particle over the seed particle. The ratio of the signal for the residue particle to the signal for the seed particle can be expressed as follows:

$$V_{grown}/V_{seed} = \frac{[D_{seed}(1+m)]^n}{(D_{seed})^n} \qquad (3)$$

Thus, $$V_{grown}/V_{seed} = (1+m)^n \qquad (4)$$

In expressions (3) and (4), $V_{grown}$ is the output pulse amplitude of the particle detector in response to the residue particle with a shell of dissolved solid, $V_{seed}$ is the output pulse amplitude of the particle detector that would be produced in response to the seed particle with no shell. The exponent n is a value depending upon the size of the particle ranging between 5 and 6.

Since m is very small, the expression for the ratio of the signals can be approximated as follows:

$$V_{grown}/V_{seed}=1+mn \quad (5)$$

Solving equation (5) for m, the following equation results:

$$m=1/n\ [V_{grown}/V_{seen}-1] \quad (6)$$

For a seed particle size of 0.343 microns, the value of n is about 5.12. If $V_{grown}$ is about 10 percent greater than $V_{seed}$, then solving equation (6) for m results in the following:

$$m=[1/5.12]\times[1.1-1]=0.0195 \quad (8)$$

In other words, the 10 percent larger signal is produced as a result of the fact that $D_{grown}$ is 1.95 percent larger than $D_{seed}$. The volume of the solid residue formed in the shell around the seed particle can be calculated as follows. The shell thickness t is:

$$t = 1/2\ [D_{grown} - D_{seed}] \quad (8)$$
$$= 1/2\ [D_{seed} \times (1+m) - D_{seed}] \quad (9)$$
$$= D_{seed} \times m/2 \quad (10)$$

The volume of the shell is the surface area multiplied by the shell thickness t. The seed particle surface area is:

$$A=\pi\times(D_{seed})^2 \quad (11)$$

Accordingly, the volume V of the shell is:

$$V = \pi t(D_{seed})^2 \quad (12)$$
$$= (\pi/2) \times m(D_{seed})^3 \quad (13)$$

Substituting for m, the volume of the shell is $$V=\pi/2\times(D_{seed})^3\ [(1/n)\times(V_{grown}/V_{seed}-1)] \quad (14)$$

The concentration of the solid C can be expressed in terms of the volume of the residue shell $V_{shell}$ and the volume of the droplet $V_{droplet}$ as follows:

$$C = V_{shell}/V_{droplet} \quad (15)$$

$$C = \frac{(\pi/2)(D_{seed})^3[(1/n)] \times [(V_{grown}/V_{seed}) - 1]}{(\pi/6)(D_{droplet})^3} \quad (16)$$

$$C = [(3/n)(V_{grown}/V_{seed} - 1)](D_{seed}/D_{droplet})^3 \quad (17)$$

in which $D_{droplet}$ is the diameter of the droplet or, in other words, in the preferred embodiment, 50 microns. Substituting the known values for equation 17, the following values result:

$$C = (3/5.12) \times (0.1) \times (0.343/50)^3 = 0.000000019 \quad (18)$$

or 19 parts per billion. Thus, a 10 percent change in the voltage signal from the particle detector will result from a concentration of 19 parts per billion. In the Hiac Royco 5230A instrument, the 0.343 micron particle will produce a 30 millivolt output signal so a 10 percent increase corresponds to 3 millivolts of signal. Three millivolts provides a signal-to-noise ratio well over 2 and, therefore, is easily detectable.

By a similar calculation, it can be shown that if a particle detector having the sensitivity to detect 0.1 micron particle and a seed particle of this size were used, then dissolved concentrations of less than 1 part per billion could be detected.

To provide continuous dynamic calibration of the system, monitor seed particles, much larger than measurement seed particles are mixed with the measurement seed particles in the seed particle reservoir 15 in a ratio of about one monitor seed particle to 100 measurement seed particles. The monitor seed particles are also latex beads, and, in a preferred embodiment, have a diameter of 1.1 microns compared to the 0.343 micron diameter measurement seed particles. The monitor seed particles are drawn into the mixer 13 along with the measurement seed particles and some of the droplets ejected by the nozzle will contain the monitor seed particles. While the residue particles produced from the droplets containing monitor seed particles would have some variation in size due to changes in the concentration in the dissolved solids in the sample liquid, this variation in size will have negligible effect because of the size of the monitor seed particle being 1.1 microns in diameter and also because a particle of this size causes the signal voltage produced by the particle detector 23 in response to the particle to occur on a flat portion of the calibration curve of the particle measuring instrument where changes in particle size cause little change in the output voltage. FIG. 5 illustrates the calibration curve for the particle detector plotting the voltage of the output pulses produced by the particle detector verses the particle diameter in microns on a logarithmic scale. In FIG. 5, the variation in the pulse amplitude with particle diameter becomes substantially flat above 1 micron.

The voltage amplitude produced from the first monitor seed particle is stored in the instrument as a benchmark voltage to provide a basis for corrections to avoid errors due to drift in the intensity of the laser beam of the particle detector 23 or in the flow rate of the particles through the particle detector 23. A change in either the intensity or the flow rate of the particle will cause a corresponding change in the signal voltage. To prevent changes in the flow rate or in the intensity of the laser beam from causing errors in the concentration measurement, measurement is calibrated in accordance with the voltage amplitude currently being generated from the residue monitor particles produced from droplets containing monitor seed particles. The ratio of this voltage to the benchmark voltage which has been stored in the instrument is then used to correct the output voltage $V_{grown}$ generated from a measurement residue particle in accordance with the following formula:

$$V''_{grown} = V_{grown} \times (V_o/V_{mon}) \tag{19}$$

in which $V'_{grown}$ is the output voltage of the particle detector corrected for drift in the flow rate and/or laser beam intensity, $V_{grown}$ is the current output voltage of the particle detector, generated from a measurement residue particle produced from a droplet containing a measurement seed particle. $V_o$ is the original signal generated by the first residue monitor particle produced from a droplet containing a monitor seed particle and stored as a benchmark voltage and $V_{mon}$ is the current signal voltage generated from the residue monitor particle obtained from a droplet containing a monitor seed particle. Thus, by using the monitor particles and equation 19, the measurements of the dissolved solids can be corrected for drift in the intensity of the laser beam in the particle detector or for drift in the flow rate of particles through the laser beam.

Figure 6:
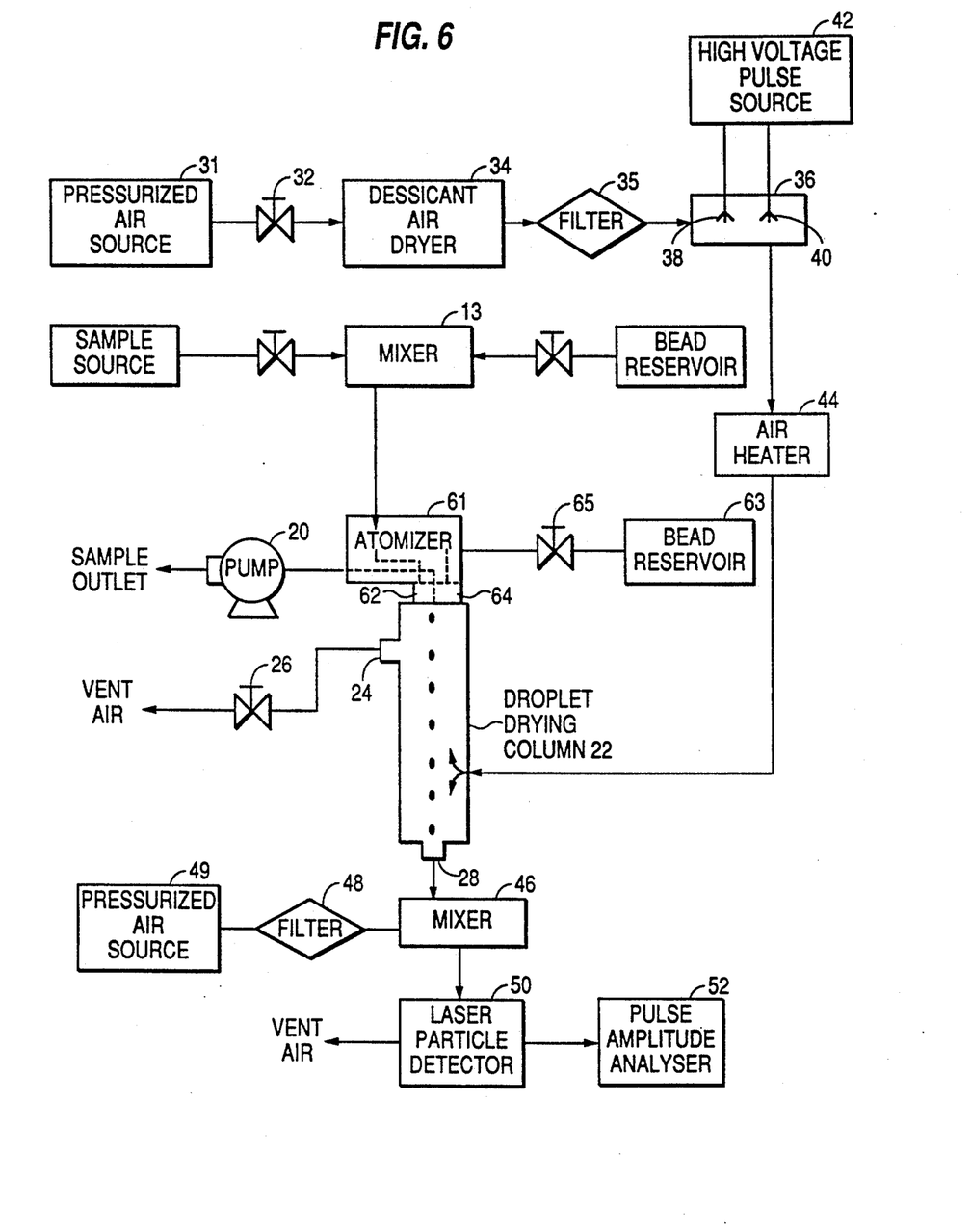
FIG. 6 schematically illustrates an alternative embodiment of the present invention using a different calibration technique.

FIG. 6 illustrates an alternative embodiment of the present invention employing an alternative system for calibrating the measurement. The embodiment of FIG. 6 is like that of FIG. 1 except that the system employs an atomizer 61 which, instead of being the same atomizer that is employed in a monochromatic ink jet printer, is the atomizer that is employed in a color printer. In this atomizer, separate chambers 62 and 64 are provided behind separate nozzles in the atomizer so that separate sources of liquid to be atomized can be directed through different nozzles. As shown in FIG. 6, chamber 62 receives the mixture of liquid sample with the 0.343 micron diameter beads from the mixer 13. A calibration bead reservoir 63 containing beads 0.343 microns in diameter in ultrapure water is connected to the second chamber 64 in the atomizer through a valve 65. The chambers 62 and 64 are located over different nozzles in the atomizer 17 and both of the chambers are connected downstream to the pump 20. When the valve 65 is open, beads mixed in ultrapure water will be drawn from the reservoir 63 through chamber 64 and ultrapure water droplets containing the calibration beads can be ejected into the drying column 22 by applying pulses to the resistors over the nozzle openings connected to the chamber 64. Each chamber in the atomizer 61 will have eight nozzles communicating with the drying column 22. The system of the present invention uses four nozzles for each chamber operated in sequence as desired in connection with the nozzle 17 in the embodiment of FIG. 1. In this manner, ultrapure water droplets containing the 0.343 micron calibration beads can be selectively ejected into the drying column. These droplets will be dried and the resulting residue particles will consist entirely of the calibration beads 0.343 microns in diameter. Accordingly, when these calibration beads pass through the particle detector 50, the resulting amplitude measurements obtained by the pulse analyzer provides a current calibration voltage representing the size of the measurement bead against which the voltage from the residue particle containing the dissolved solid shell can be directly compared to obtain an accurate size measurement.

As described above, a known amount of added material is provided to each droplet very conveniently by providing the bead of a known diameter in each droplet. However, the same effect can be achieved by mixing in the known amount per unit volume of a dissolvable material in the liquid before the liquid is transported to the atomizer for being atomized into droplets. In this latter arrangement, the resulting residue particles will not consist of a bead with a surrounding shell of the dissolved solid material. Nevertheless, the increase in size of the residue particles over that which would result from the added material alone will be the same as that for when the added material was in the form of beads.

This and other modifications may be made to the above-described specific embodiments of the invention without departing from the spirit and scope of the invention which is defined in the appended claims.

I claim:

1. A method of measuring minute concentrations of a solid dissolved in a liquid comprising mixing a known amount of seed material into said liquid, atomizing said liquid into droplets including a measurement droplet of a known size containing a known amount of said seed material, drying said measurement droplet to a residue particle containing said solid and said seed material in solid form, and measuring the size of said residue particle.

2. A method of measuring minute concentrations of dissolved solids in a liquid comprising mixing a solid seed particle of a known size with said liquid, atomizing said liquid into droplets including a measurement droplet of a known size containing said seed particle, drying said measurement droplet to a residue particle consisting said seed particle and a shell of said solid material around said seed particle, and measuring the size of said residue particle.

3. A method of measuring minute concentrations of a solid dissolved in a liquid as recited in claim 2, wherein said step of measuring the size of said residue particle comprises passing said residue particle through a light beam to scatter light from said particle, detecting light scattered from said particle to generate a pulse and measuring the amplitude of said pulse.

4. A method as recited in claim 2, further comprising mixing a multiplicity of solid seed particles of known size with said liquid prior to atomizing said liquid into said droplets so that a multiplicity of said droplets contain seed particles, drying said multiplicity of droplets to a multiplicity of residue particles, and measuring the size of the particles of the multiplicity of residue particles.

5. A method as recited in claim 4, wherein the step of measuring the size of said residue particles comprises passing said residue particles through a light beam one at a time to scatter light from each of said particles, and detecting light scattered from each of said particles to generate a pulse, and measuring the amplitude of each pulse.

6. A method as recited in claim 5, wherein a first set of said seed particles have a first predetermined size and a second set of said particles have a second predetermined size substantially larger than said first predetermined size, the size of said second set of particles being selected so that the amplitude of pulses produced from residue particles including seed particles of said second set do not vary substantially with changes in the concentration of dissolved solids in said liquid.

7. A method as recited in claim 6, wherein the seed particles of said second set have a diameter of about 1.1 microns.

8. A method as recited in claim 5, further comprising atomizing an ultrapure liquid containing a multiplicity of solid calibration seed particles of known size into calibration droplets, drying said calibration droplets to residue calibration particles consisting of said calibration seed particles, passing said calibration residue particles through said light beam to scatter light from said calibration residue particles, detecting light scattered from said calibration residue particles to generate calibration pulses and measuring the amplitude of calibration pulses.

9. A method as recited in claim 4, wherein said droplets are dried by injecting said droplets into a column in a direction to pass axially through said column and passing drying air over said droplets in said column in a reverse direction to the direction of movement of said droplets in said column to separate smaller satellite droplets from said droplets of a constant size.

10. A method as recited in claim 9, wherein said drying air is ionized to neutralize static charges on said droplets.

11. A method as recited in claim 2, further comprising atomizing an ultrapure liquid containing a second solid seed particle of a known size into droplets including a calibration droplet containing said second seed particle, drying said calibration droplet to a second residue particle consisting of said second seed particle and measuring the size of said second residue particle.

12. An apparatus for measuring minute quantities of a solid dissolved in a liquid comprising means to mix solid seed particles of a known size with said liquid, atomizing means to atomize the mixture of said liquid and said seed particles into droplets of a known size wherein some of said droplets contain a single seed particle, means to dry said droplets to residue particles comprising said seed particles surrounded by a shell of said solid material, means to measure the size of said residue particles.

13. An apparatus as recited in claim 12, wherein said means to atomize the mixed liquid and particles into droplets comprises means defining a nozzle aperture and a chamber behind said aperture to receive said mixed liquid and particles and means to generate a bubble in said chamber behind said nozzle to eject a droplet out of said nozzle.

14. An apparatus for measuring dissolved solids in a liquid as recited in claim 12, wherein said means to dry said droplets to residue particles comprises a column, said atomizing means ejecting said droplets into said column to pass axially through said column in a first direction, means to introduce drying gas into said column to pass over said droplets in the reverse direction from said first direction.

15. An apparatus for measuring dissolved solids in a liquid as recited in claim 14, wherein said drying gas is introduced into said column midway between its ends to travel through said column in said reverse direction in part of said column and in said first direction in part of said column to carry said residue particles out of said column.

16. An apparatus for measuring minute dissolved solids in a liquid as recited in claim 14, further comprising means to ionize said gas prior to introducing said gas in said column.

17. An apparatus as recited in claim 12, wherein said atomizing means comprises a plurality of nozzles each communicating with a separate chamber in said atomizing means, means to introduce said mixture of said liquid and seed particles into a first one of said chambers to be ejected in droplets from the nozzle communicating with said first one of said chambers, and means to introduce into a second one of said chambers ultrapure liquid containing solid calibration seed particles of a known size, said atomizer having means to generate a bubble in said ultrapure liquid behind the said second nozzle to eject a calibration droplet of said ultrapure liquid through said second nozzle opening, said drying means operating to dry said calibration droplets to calibration residue particles, said means to measure the size of said particles comprising means to measure the size of said calibration residue particles.

18. An apparatus as recited in claim 17, wherein said measuring means comprises a laser beam and means to direct said residue particles including said calibration residue particles through said laser beam one at a time to scatter light from said residue particles, photoelectric means to detect the light scattered from said residue particles to generate a pulse in response to each residue particle and means to measure the amplitude of each pulse generated by said photoelectric means.

* * * * *